United States Patent [19]

Osawa et al.

[11] Patent Number: 4,675,295

[45] Date of Patent: Jun. 23, 1987

[54] PROCESS FOR PRODUCING SUBCULTURABLE LYMPHOKINE-PRODUCING HUMAN T CELL HYBRIDOMAS

[75] Inventors: Toshiaki Osawa, Tokyo; Yoshiro Kobayashi, Chiba; Makoto Asada; Masahiro Higuchi, both of Tokyo, all of Japan

[73] Assignee: Denki Kagaku Kogyo Kabushiki Kaisha, Tokyo, Japan

[21] Appl. No.: 574,213

[22] Filed: Jan. 26, 1984

Related U.S. Application Data

[63] Continuation-in-part of Ser. No. 437,375, Oct. 28, 1982, abandoned.

[30] Foreign Application Priority Data

Oct. 28, 1981 [JP] Japan .............................. 56-171505
Apr. 11, 1983 [JP] Japan .............................. 58-63442

[51] Int. Cl.$^4$ .................... C12N 15/00; C12N 5/00; C12P 21/00
[52] U.S. Cl. ................... 435/172.2; 435/68; 435/240; 935/99; 935/101
[58] Field of Search ............ 435/68, 172.2, 240, 435/241, 948; 436/548; 424/85; 935/99, 101

[56] References Cited

U.S. PATENT DOCUMENTS 4,276,282 6/1981 Sugimoto et al. ................ 435/68
4,383,036 5/1983 Sugimoto et al. ................ 935/99

FOREIGN PATENT DOCUMENTS 0057107 8/1982 European Pat. Off. .

OTHER PUBLICATIONS

Adams et al., "Leukemia: Serial Transplantation of Human Leukemic Lymphoblasts in the Newborn Syrian Hampster", Cancer Research, 27, pp. 772–783 (1967).

Watanabe et al, "Transplantability of Human Lymphoid Cell Line, Lymphoma and Leukemia in Splenectomized and/or Irradiated Nude Mice", Cancer Research, 40, pp. 2588–2595 (1980).

Grillot–Courvalin et al., "Establishment of Human T–Cell Hybrid Line with Suppressive Activity, Nature, vol. 292, pp. 244–845, 1981.

Grollman, A., "Inhibitors of Protein Biosynthesis", J. of Biol. Chem., vol. 243, pp. 4089–4094, 1968.

Merck Index, Ninth Ed., 1976.

Gillis et al., "Biochemical and Biological Characterization of Lymphocyte Regulatory Molecules", J. Exp. Med., vol. 152, pp. 1709–1719 (1980).

Wright, "Isolation of Heterokaryons and Hybrids by a Selective System", Ex. Cell. Res., vol. 112, pp. 395–407 (1978).

Rocklin, R., "Mediators of Cell Immunity", in Basic and Clinical Immunology (Fudenberg, Ed.) 1978, p. 128.

Hochster et al, "Metabolic Inhibitors", Academic Press, 1963, pp. 30–45.

Primary Examiner—Charles F. Warren
Assistant Examiner—John E. Tarcza
Attorney, Agent, or Firm—Sughrue, Mion, Zinn, Macpeak & Seas

[57] ABSTRACT

A process for preparing human T cell hybridomas which are subculturable and produce lymphokines comprising the steps of: (1) treating a human acute leukemia cell with a protein and/or RNA synthesis inhibitor; (2) independently activating a human T cell with a mitogen or antigen; (3) fusing the thus-treated human acute leukemia cell with the thus-activated human T cell in the presence of a fusion accelerator; and (4) isolating the thus-formed hybridoma. An in vivo process for producing lymphokines using the hybridomas is also described.

25 Claims, No Drawings

PROCESS FOR PRODUCING SUBCULTURABLE LYMPHOKINE-PRODUCING HUMAN T CELL HYBRIDOMAS

CROSS REFERENCE

This is a continuation-in-part application from Ser. No. 437,375 filed Oct. 28, 1982, now abandoned.

BACKGROUND OF THE INVENTION

The present invention relates to subculturable lymphokine-producing human T cell hybridomas and a process for the preparation thereof. More particularly, it relates to subculturable lymphokine-producing human T cell hybridomas obtained by the cell fusion of a protein synthesis inhibitor and/or an RNA synthesis inhibitor-treated human acute leukemia cells and mitogen- or antigen-activated a human T cells in the presence of a fusion accelerator, and a process for the preparation thereof. Also, the present invention relates to a process for preparing lymphokine which comprises transplanting a lymphokine-producing human T cell hybridoma to a warm-blooded animal other than human, multiplying said hybridoma in said animal and, cultivating multiplied hybridomas in a nutrient medium.

The phenomenon of cell fusion was discovered by Y. Okada using Sendai virus (HVJ) (Y. Okada, Biken J., 1: 103 (1958)). Since the discovery of Sendai virus mediated cell fusion, this method has been greatly used in the development of the field of somatic cell genetics.

In 1975, Kohler and Milstein succeeded in utilizing the cell fusion technique in the field of immunology. That is, it was first reported in G. Kohler and C. Milstein, Nature, 256: 495 (1975) that the fusion of spleen cells obtained from immunized mice with HAT (hypoxanthine-amino- pterin-thymidine)-sensitive murine myeloma cells results in the formation of hybridomas capable of permanently producing a monoclonal antigen-specific antibody.

Lymphocytes contained in human and animal immune systems are divided broadly into cells from thymus (T cells) and cells from bone marrow (B cells).

B cells are antibody-secreting cells. The cell fusion reported by G. Kohler et al. is between mouse-derived B cells and HAT-sensitive murine myeloma cells. On the other hand, T cells are formed by differentiation and maturation of stem cells from the bone marrow in the thymus. Further, T cells circulate in the blood flow through peripheral organs such as lymph nodes and the spleen.

T cells play a significant role in controlling the immune response of a living body. It is well known that the immune response-controlling function of T cells is promoted by a soluble mediator generally called a lymphokine which is released by T cells (H. G. Kunkel and F. J. Dixon, *Advances in Immunology,* 29: 56 (1980), Academic Press).

Various attempts have heretofore been made to cure various diseases, such as cancer, allergy, and infectious diseases, by controlling the immune response of a living body. Lymphokine which is specific to various immune cells may be used as a more effective immunotherapeutic agent and is expected to be utilized widely in the medical field as a clinical diagnostics (Bernstein, I. D., D. E. Thor, B. Zbar and H. J. Rapp: *Science* 172 729 (1971) and Piessens, W. F. and W. H. Churchill: *J. Immunol* 114 293 (1975)). Thus, lymphokine is a medically very important substance.

In accordance with conventional methods, however, it is impossible to prepare a large amount of lymphokine, and furthermore the purity of the lymphokine that has been conventionally prepared in the past is low. Thus the utilization of lymphokine in the medical field has been seriously inhibited.

Lymphokines are non-antibody protein factor groups which are produced by lymphocytes due to, for example, an antigen-specific stimulus or mitogen stimulus. Further, lymphokines are produced mainly by T cells. Typical lymphokines and their actions are shown below:

1. Lymphokines acting on macrophages
   (1) Migration inhibitory factor (MIF)
       Action: prevents the migration of macrophages in vitro
   (2) Macrophage activating factor (MAF)
       Action: stimulates phagocytosis, the bactericidal action, etc. of macrophages
   (3) Monocyte-macrophage chemotactic factor (MCF)
       Action: causes chemotaxis of monocyte macrophages
2. Lymphokines acting on polymorphonuclear leucocytes
   (1) Leucocyte-migration inhibitory factor (LIF)
       Action: prevents the migration of polymorphonuclear leucocytes in vitro
   (2) Chemotactic factor
       Action: causes chemotaxis of neutrophil, eosinophil and basophil leucocytes
3. Lymphokines acting on lymphocytes
   (1) Interleukin II (IL-II)
       Action: stimulates the division and proliferation of T cells activated by an antigen or mitogen
4. Lymphokines acting on other cells
   (1) Lymphotoxin (LT)
       Action: damages and peels apart L cells and HeLa cells in vitro
   (2) γ-Interferon (IFN-γ)
       Action: interferes with virus pathogenicity
   (3) Colony stimulating factor (CSF)
       Action: acts on bone marrow lymphocyte precursor cells (GFU-C), accelerating their differentiation and proliferation into granulocytes or macrophages The activity of the above-described lymphokines is measured in vitro. It is reported, however, that there are lymphokines whose activity, as exhibited in vitro, is recognized to correspond to that as exhibited in vivo. For example, MIFs are presumed to inhibit migration of macrophages (Takeo Kuroyanagi et al: "Lymphokine" *Shin Meneki Kagaku Sosho* vol. 6, p. 33, Igakushoin Co., Ltd., Tokyo (1979)).

In addition, in teleangiectatic edema, caused by a chemical mediator in, for example, a tuberculin reaction, a large accumulation of macrophages is observed. This is because the macrophages, which migrate and collect as a result of MCF derived from sensitized T cells, are further fixed by MIF. This demonstrates the correlation between MCF and MIF with living body immunological defenses and thus permits efficient treatment of foreign substances by effective accumulation and activation of macrophages.

Lymphokines which can be expected to be used as medicines in the future include MAF, lymphotoxin, interleukin II, IFN-γ, and CSF, as well as MCF and MIF.

Typical methods of preparing lymphokines include (1) cultivating peripheral blood lymphocytes sensitized by an antigen together with the antigen (D. J. Cameron and W. H. Churchill: *J. Clin. Invest.* 63 977 (1979)); (2) cultivating peripheral blood lymphocytes or spleen cells together with a mitogen (Weiser, W. Y., Greineder, D. K., Remold, H. G. et al: *J. Immunol.*, 126 1958 (1981)); and (3) establishing an antigen-specific T cell clone by the use of T cell growth factor (IL-II) and cultivating the clone (Green, J. A., S. R. Cooperband and S. Kibrick: *Science* 164 1415 (1969)).

Methods (1) and (2) above need a large amount of blood and enable one to prepare only a limited amount of lymphokine. Therefore, it is difficult to prepare a large amount of pure lymphokine according to methods (1) and (2). In accordance with method (3), specific lymphokines can be prepared in the presence of IL-II. However, method (3) suffers from disadvantages in that the production of lymphokines from T cells is poor and it is difficult and expensive to obtain human IL-II.

The above-described problems are encountered when using the conventional methods because lymphokine-producing T cells cannot be subcultivated and their growth is poor even if they are cultivated in the presence of a growth factor, such as IL-II. Thus, it is very difficult at the present time to produce a sufficient amount of lymphokine for clinical use.

As a means of solving the above-described problems using the cell hybridization technique, T cell hybridomas for mice have already been established (Taniguchi, M., Saito, T. and Tada, T.: *Nature* 278 555–558 (1979)). Therefore, it is now possible to analyze lymphokines produced by these cells. However, such lymphokines produced by murine T cell hybridomas cannot be used for human clinical purposes. From the viewpoint of human immunology and necessity of clinical application, it has been desired to establish lymphokine-producing human T cell hybridomas which are subculturable.

It is reasonable to expect that the same method as used for the murine T cell fusion can be applied to the fusion of human T cells. Indeed, there is a method where lymphokine-producing T cells (not subculturable) and HAT (hypoxanthine-aminopterin-thymidine)-sensitive T line tumor cells (subculturable) have been fused in the presence of fusion accelerator. Therefore, only those cells which could grow on a HAT medium were screened and cloned to obtain the desired lymphokine-producing T cell hybridomas (see Catherine Grillot-Courvalin et al., *Nature* 292: 844 (1981)).

However, a very complicated and difficult process is required for providing HAT-sensitivity to human T line tumor cells.

SUMMARY OF THE INVENTION

Therefore, an object of the present invention is to provide a process for preparing human T cell hybridomas which are subculturable and produce lymphokines.

Another object of the present invention is to provide a process for producing lymphokines suitable for a large scale production.

As a result of extensive investigations to develop a method of preparing subculturable lymphokine-producing human T cell hybridomas, it has been found that such human T cell hybridomas are obtainable by the cell fusion of a protein synthesis inhibitor- or a combination of protein synthesis inhibitor and an RNA synthesis inhibitor-treated human acute leukemia cells with mitogen- or antigen-activated human T cells in the presence of a fusion accelerator.

Therefore, the present invention provides a process for preparing a subculturable lymphokine-producing human T cell hybridoma which comprises treating a human acute leukemia cell with a protein synthesis inhibitor or a combination of a protein synthesis inhibitor and an RNA synthesis inhibitor, while independently activating a human T cell with a mitogen or antigen, fusing the thus-treated human acute leukemia cell with the thus-activated human T cell in the presence of a fusion accelerator, and then isolating the thus-formed hybridoma.

DETAILED DESCRIPTION OF THE INVENTION

The process of the present invention generally comprises the following steps (A), (B), (C), (D) and (E).

Step (A)

Lymphocytes separated from human peripheral blood and the spleen or thymus which have been aseptically excised by an operation are activated with a mitogen or antigen. Thereafter, the mitogen or antigen bound to the cells is removed so that there is as low a level of mitogen or antigen present as possible.

Any antigen or mitogen can be used in the present invention as long as it is a substance capable of inducing the transformation of human T cells, and it is selected appropriately depending on the type of lymphokine desired. Examples of such mitogens include phytohemagglutinin-P (PHA-P) and concanavalin A (Con A). Examples of useful antigens include PPD (purified protein derivative, i.e., purified tuberculin protein), bacterial toxoid, viral antigens and SK-SD (streptokinase-streptodornase). Generally, PHA-P induces lymphokines such as LT, MIF, MAF and CSF, Con A lymphokines such as LT, MIF and MAF, and PPD lymphokines such as MIF, IL-II and IFN-γ.

Step (B)

Human acute leukemia cells are treated with a protein synthesis inhibitor or a combination of a protein synthesis inhibitor and an RNA synthesis inhibitor. Thereafter, the inhibitor contained in the culture medium is removed by centrifugation.

Human acute leukemia cells which can be used in the present invention include T cell line tumor cells, such as CEM (ATCC No. CCL-119), TALL (The Pharmaceutical Department of Tokyo University, Tokyo, Japan) and MOLT-4 (The Pharmaceutical Department of Tokyo University, Tokyo, Japan).

As protein synthesis inhibitors, known protein synthesis inhibitors for eukaryotic cells which can inhibit protein synthesis irreversibly can be used. Emetine hydrochloric acid salt and pactamycin are preferred protein inhibitors for use in the present invention. The protein synthesis inhibitors can be used alone or in combination with RNA synthesis inhibitors. Examples of such RNA synthesis inhibitors include α-amanitin, adriamycin and the like. A preferred RNA synthesis inhibitor for use in the present invention is actinomycin D.

The treatment of human acute leukemia cells with the protein or RNA synthesis inhibitors is performed under conditions such that both division and growth of the cells are completely prevented. For example, when CEM ($2 \times 10^6$ cells/ml) is treated at 37° C. for 2 hours with emetine hydrochloric acid salt alone, the concentration of the salt is from $10^{-4}$ to $10^{-5}$M, and when the salt is used in combination with actidmycin D, the concentrations of the salt and actinomycin D are preferably $10^{-4}$ to $10^{-5}$M and 0.05 to 2.0 μg/ml, respectively.

Step (C)

The above-prepared lymphokine-producing human T cells and human acute leukemia cells whose growth has been inhibited by a protein synthesis inhibitor or a combination of a protein synthesis inhibitor and an RNA synthesis inhibitor are fused in the presence of a suitable fusion accelerator.

The ratio of number of cells of human T cells to human acute leukemia cells in the fusion step is from 1:1 to 20:1 and preferably from 2:1 to 15:1.

Fusion accelerators which can be used in the present invention include polyethylene glycol (PEG), polyvinyl alcohol, and viruses having a cell-fusion ability, particularly paramyxovirus to which Sendai virus (HVJ) belongs, and its inactivated product. Generally, PEG having a molecular weight of from 1,000 to 4,000 is used.

Step (D)

Living cells of the above-obtained fused cells are concentrated to $10^5$ to $2 \times 10^6$ cells/ml and incubated on a 96 well culture plate containing a nutrient medium with a feeder layer added thereto.

As feeder layers, human cells whose growth has been inhibited by antibiotics such as mitomycin C or by irradiation with X rays are used.

Any nutrient medium can be used as long as it is a medium on which human acute leukemia cells can grow. For example, a medium prepared by adding 10% fetal calf serum (FCS), $5 \times 10^{-5}$M 2-mercaptoethanol, and 2 mM glutamine to RPMI 1640 (Nissui Seiyaku Co., Ltd.) is suitable to use.

One week after cultivation, the human acute leukemia cells and the feeder layer treated with the inhibitor completely die and the fused cells remain, i.e., continue to grow.

In order to confirm the formation of fused cells, known techniques ar employed for (1) an analysis of cell surface antigens and (2) analysis of cell karyotypes.

Step (E)

The cultivation supernatant of a well in which the fused cells have grown is analyzed to confirm production of the desired lymphokine.

The thus-prepared fused cells can be subcultivated for a long period of time while maintaining the lymphokine activity. Furthermore, cloning enables one to obtain a subline efficiently producing lymphokine.

Lymphokines can be produced by cultivating the subline in vitro. This cultivation can be performed by known techniques. Examples of in vitro cultivation methods include a stirring cultivation method and a stationary cultivation method using a Petri dish and a Roux flask.

However, when it is desired to obtain lymphokines in large quantities by the aforesaid in vitro method is undesirable because large amount of expensive animal sera and growth factor are required for cultivating a lymphokine-producing human T cell hybridoma, lymphokine producibility is lowered due to repeated cultivation, etc. so that it is extremely difficult to supply lymphokines in large quantities at low costs.

Further extensive investigations on a process for obtaining lymphokines in large quantities have led to a process for obtaining lymphokines which comprises transplanting the lymphokine-producing human T cell hybridoma prepared as described above to warm-blooded animals other than humans, multiplying the hybridoma in the animals, taking the thus-multiplied cells out of the animals and, cultivating the hybridomas in a nutrient medium.

A process which comprises transplanting normal animal cells or tumor cells to warm-blooded animals other than humans and multiplying the cells in the animals and a process which comprises producing a physiologically active substance from multiplied cells are described in, for example, the following publications: Japanese Patent Publication Nos. 41230/81, 54158/81, etc.; Adams, R. A., G. E. Foley, B. G. Uzman, S. Farber, H. Lazarus and L. Kleinman, *Cancer Research*, 27, 772 (1967); Jiro Imanishi, *Tanpakushitsu, Kakusan, Koso* (*Proteins, Nucleic Acids and Enzymes*), separate volume, No. 25, page 16 (1981, December); Miyoshi, I., I. Kubonishi, H. Uchida, S. Hiraki, Y. Hatsuda, T. Tanaka, H. Masui and K. Hiraki, *International Journal of Cancer*, 18, 67 (1976), etc.

However, there is no report that a lymphokine-producing human T cell hybridoma line, particularly, a subculturable lymphokine-producing human T cell hybridoma prepared by the process disclosed herein is cultured by the aforesaid process to prepare lymphokines.

The lymphokine-producing human T cell hybridoma is transplanted to a warm-blooded animal other than human and multiplied in the animal and the multiplied hybridoma is taken out of the animal and cultured in a nutrient medium to obtain a lymphokine.

Examples of warm-blooded animals which can be used in the present invention include animals other than humans in which lymphokine-producing human T cell hybridoma lines can be multiplied, such as, nude mice, nude rats, hamsters, chickens, mice, rats, etc. From the viewpoints of multiplication of lymphokine-producing human T cell hybridoma lines, stability of lymphokines in the animals, etc., hamsters, particularly golden hamsters to which an immunosuppressive agent was administered prior to or after transplantation of hybridomas, are preferred. As immunosuppressive agents, cortison acetate, cyclophosphamide or anti-lymphocyte sera obtained by immunizing rabbits with hamster thymus cells, etc. can be employed.

The process for preparing lymphokines which comprises multiplying a lymphokine-producing human T cell hybridoma line in a hamster to which an immunosuppressive agent was administered and then cultivating the hybridomas in a nutrient medium is explained below.

A suspension of $10^5$ to $10^8$ cells of lymphokine-producing human T cell hybridoma line in a physiological saline solution (hereafter simply referred to as saline) is subcutaneously or intraperitoneally administered to autopropagated neonatal hamsters (weighing 2 to 4 g in average) within 24 hours after birth. Then, anti-lymphocyte serum prepared by sensitizing rabbits with hamster thymus cells in accordance with, e.g., the method of S. S. Tevethia et al (Tevethia, S. S., G. R. Dreesman, N. L. Robert and F. Rapp: *Journal of Immunology*, 101, 1105 (1968), is administered at the dose of 0.01 to 0.2 ml, or a drug such as cortison acetate, cyclophosphamide, or the like, is administered at the doses of 0.02 to 0.2 mg and 10 to 50 mg, respectively, per kg of the body weight. The immunosuppressive agent is given every two or three other days until a tumor mass is taken out from the animal. After inoculating hybridomas, the hamsters are fed for 7 to 40 days. Feeding and control can be performed in a manner similar to feeding of normal hamsters. A period of feeding varies depending upon cell count to be inoculated and stability of cells but 20 to 30 days are generally preferred because the yield of viable cells is high.

The cell mass which has grown to a shape like a lump is aseptically excised, cut into small pieces, passed through a stainless steel mesh and suspended in a phosphate buffer solution (hereafter simply referred to as PBS). The cells are employed for preparation of lymphokines, transplantation to another hamster and freeze storage. The total count of viable cells contained in the cell mass is in the range of $5 \times 10^9$ to $5 \times 10^{10}$.

The cells suspended in PBS is centrifuged (1000 rpm, 5 minutes). The supernatant is discarded and a nutrient medium is added.

Nutrient media are appropriately chosen from a basal medium containing at least one member selected from the group consisting of sugars, amino acids, vitamins, hormones, proteins, antibiotics, growth factors and inorganic salts, etc., or a medium obtained by adding animal serum, an antigen, a mitogen, etc. to the basal medium.

As basal media, an RPMI 1640 medium commercially available, an MEM medium, a Dulbecco-modified MEM medium, etc. can be employed.

As animal sera, calf fetal sera, neonatal calf sera, calf sera, horse sera, or human sera can be added to the basal medium in an amount of 1 to 20% by weight.

As antigens, purified tuberculin (PPD), diphteria toxoid, herpes virus, etc. can be employed.

As mitogens, phytohemagglutinin (PHA), concanavalin A (ConA), staphylococcal enterotoxin A (SEA), or galactose oxidase (GO) can be employed.

A lymphokine-producing human T cell hybridoma line which has been adjusted to $10^5$ to $10^7$ cells/ml in the nutrient medium is cultivated at 37° C. in a flask for tissue culture or a spinner flask in an atmosphere of 5% $CO_2$ and 95% air. The cultivation time varies depending upon the composition of the medium and initial concentration of the cells but is suitably in the range of 2 to 72 hours.

After centrifuging (1000 rpm, 5 minutes) the culture solution, i.e., the supernatant is separated from cells. The supernatant is provided for determination of a lymphokine activity by the method later described in Examples 6 to 10, as is, or after purifying the supernatant by means of dialysis, salting out with ammonium sulfate, ion exchange chromatography, gel filtration, etc. The cells are extracted with a buffer such as PBS or water and the extract is provided for determination of a lymphokine activity by the method later described in Examples 6 to 10, as is, or after purifying by means of dialysis, salting out with ammonium sulfate, ion exchange chromatography, gel filtration, etc.

Subculturable lymphokine-producing human T cell hybridomas are useful for the mass production of lymphokines and, furthermore, since the desired lymphokine-producing cells are obtainable in a large amount, they can be utilized as an extraction source for lymphokine-production related genes (e.g., messenger RNA (mRNA)) contained therein. It is also possible that after the preparation of complement DNA (cDNA) from the extracted mRNA by the use of a reverse transcriptase, the lymphokines can be prepared using microorganisms (e.g., bacteria, yeasts, actinomycetes, and fungi) according to conventional genetic recombination techniques.

The following examples are given to illustrate the invention in greater detail.

EXAMPLE 1

(1) Preparation of Lymphokine-Producing Human T Cell Hybridomas

Human peripheral blood lymphocytes (hereafter simply referred to as PBL) (HLA-A2, -Aw24, -B7, -Bw35, -Cw3, -Cw7) ($10^6$ cells/ml) were activated with 5 μg/ml of phytohemagglutinin-P (PHA-P, manufactured by Sigma Co., Ltd.) in RPMI1640 medium (Nissui Seiyaku Co., Ltd.) containing 10% fetal calf serum, $5 \times 10^{-5}$M 2-mercaptoethanol, and 2 mM glutamine (hereinafter referred to merely as an "RPMI medium") for 2 days. Thereafter, PHA-P bound to the cells was removed so that there was as low a level of PHA-P present as possible.

$10^{-5}$M emetine hydrochloride (manufactured by Nakarai Chemical Co, Ltd.) was added to human acute leukemia cells, CEM (HLA-A1, -Aw30, -B8, -B40) ($2 \times 10^6$ cells/ml) which had been grown on RPMI-1640 medium (containing 10% newborn calf serum). After treatment at 37° C. for 2 hours, the emetine hydrochloride contained in medium was removed by centrifugation.

The above-prepared PBL and CEM were mixed in a ratio of 10:1, and the mixture was then centrifuged to obtain cell pellets.

Cell fusion was performed at 37° C. for 45 seconds by the addition of 0.5 ml of 46% polyethylene glycol (PEG-1540 (Wako Chemical Co., Ltd.)), 15% dimethylsulfoxide (Wako Chemical Co., Ltd.), and 5 μg/ml poly-L-arginine (MW: 60,000, Sigma, St. Louis, MO). Next, 10 ml of MEM medium containing 25 mM N-2-hydroxyethylpiperazine-N'-2-ethanesulfonic acid (HEPES, Wako Chemical Co., Ltd., Tokyo, Japan) buffer was added slowly, and the resulting mixture was centrifugated and resuspended with RPMI medium to a cell density of $2 \times 10^5$ cells/ml.

After the cell fusion, the number of living cells was concentrated to $2 \times 10^5$ cells/ml and cultivated on a 96-well culture plate containing 0.2 ml of RPMI medium per well, the RPMI medium containing as a feeder layer CEM ($8 \times 10^4$ cells/ml) which had been treated with 25 μg/ml of mitomycin C at 37° C. for 30 minutes. For one week after the start of cultivation the medium was changed daily in order to moderate the influences exerted by substances released from the CEM layer.

Lymphokine activity was measured by the method as described below in (2) using hybridomas contained in a well in which their proliferation was observed.

Emetine-treated CEM and mitomycin-treated CEM used as controls completely died within one week.

(2) Cultivation of Hybridomas and Lymphotoxin Activity

Hybridomas as obtained in (1) above were cultivated in RPMI medium for one day in the presence of 20 μg/ml PHAP. Measurement of lymphotoxin activity in the supernatant with L-P3 (subline of L cells) as a target cell showed that two hybridomas (E-10, F-8) had activity. This activity was maintained for more than three months. The lymphotoxin activity was measured using the method described by Y. Kobayashi, *J. Immunology*, 122: 791 (1979). That is, a specimen (25 μl) and 25 μl of actinomycin D (4 μg/ml) was added to 50 μl of L-P3 ($3 \times 10^4$ cells) which had been formed in advance on a microplate, and were cultivated at 37° C. for 20 to 24 hours. Thereafter, the cells were fixed with glutaraldehyde and dyed, and cells which were morphologically normal were counted.

(3) Characteristics of Hybridomas E-10 and F-8

(A) Analysis of Cell Surface Antigen (1) It is known, by an analysis using a fluorescence activated cell sorter, that CEM does not react with monoclonal antibody OKT3, but that human T cells react with OKT3. Utilizing these findings, the OKT3 reactivity of human T cell hybridomas (E-10 and F-8) was examined by the two-step binding assay and immunofluorescence test using $^{125}$I-protein A. As a result, it was found that CEM had no reactivity, whereas E-10 and F-8 had reactivities which were, respectively, nearly equal to that of PBL-T cell and about 50% of PBL-T cell.

(2) The HLA antigen for E-10 and F-8 was examined by the two-step binding assay using 125I-protein A. It was found that PBL was HLA-A2 and -Bw35 positive, CEM was HLA-A1 and -B8 positive, but that both E-10 and F-8 were HLA-A1, -A2, and -B8 positive.

(B) Karyotype Analysis

The number of chromosomes in CEM, E-10 and F-8 was measured in 50 to 80 metaphase nuclei. CEM contained 84.3±0.9 (mean value ±S.D.) (median of 85) chromosomes. F-10 contained 95.5±1.7 (median of 94) chromosomes. F-8 contained 91.5±1.7 (median of 93) chromosomes. Thus, an increase in the number of chromosomes of about 10 was observed in both E-10 and F-8.

EXAMPLE 2

Lymphokine-producing hybridoma cell line E-10 ($10^6$ cells/ml) as obtained in Example 1 was cultured on RPMI medium for one day. The culture supernatant was then diluted four times. The MIF activity of the four timediluted solution was measured by the Harrington method described in J. T. Harrington, Jr. et al., *J. Immunology*, 10: 752 (1973). The macrophage migration inhibition rate was found to be 29.9% for E-10. No activity was observed for the culture supernatant of CEM which had been cultured under the same conditions. The culture supernatant as obtained by culturing PBL ($10^7$ cells/ml) on MEM medium containing HEPES buffer containing Con A (10 μg/ml) for one day showed a macrophage migration inhibitory rate of 25.2%. E-10 maintained MIF activity for more than 6 months.

EXAMPLE 3

$5 \times 10^{-5}$ M emetine hydrochloric acid salt and 0.1 μg/ml actinomycin D was added to CEM at 37° C. for 2 hours. The thus-treated CEM was fused with PBL had been prepared in the same manner as in Example 1 and was cultured in the same manner as in Example 1. Emetine hydrochloric acid salt and actinomycin D-treated CEM completely died, and only hybrid cells were observed to multiply.

The thus-obtained hybridoma cell line was cultivated in the same manner as described in Example 1-(2) and the lymphotoxin activity of the resulting supernatant was measured. It was observed that two hybridoma cell lines (C-5, D-9) had LT activity.

EXAMPLE 4

Lymphokine-producing hybridoma cell line E-10 as obtained in Example 1 was subcloned by the limited dilution method (0.5 cell/well) in RPMI-1640 medium containing as a feeder layer CEM ($2 \times 10^5$ cell/ml) which had been treated with mitomycin C as in Example 1 and also containing 20% of concanavalin A-activated PBL supernatant to obtain subline E10-20.

The E10-20 cells thus obtained were cultivated on an RPMI medium ($10^6$ cells/ml) for one day and the resulting supernatant has precipitated by ammonium sulfate (50 to 100% saturation) and dialyzed against sodium phosphate buffer containing 0.15M NaCl (PBS, pH 7.2) to obtain a test sample. The MIF activity of the sample was measured in the same manner as in Example 2. The macrophage migration inhibition rate was found to be 29.9%.

Further, the MAF activity of the sample was measured according to a process described below which is a modification of H. W. Murray et al method (*J. Exp. Med.* 153 1690 (1981)), i.e., a process in which human macrophage-like cell line U937 (The Pharmaceutical Department of Tokyo University, Tokyo, Japan) is reacted with MAF and release of $O_2^-$-(super oxide anion) is detected. That is, substantially the same procedure as Murray et al method was repeated except that 100 μl of human macrophage-like cell line U937 ($5 \times 10^5$ cells/ml) was incubated for 48 hours in the presence or absence of the test sample. As a result, 30% of the total U937 cells were shown to release $O_2^-$ in the cells, which demonstrates that the test sample contained MAF.

In the same manner as above, CEM cell line was cultivated and the culture supernatant was precipitated with ammonium sulfate (50 to 100% saturation) and dialyzed against PBS to obtain another test sample. The MIF activity of this ample was measured in the same manner as above and revealed to be 9.9%. Also, the MAF activity was measured in the same manner as above and 21% of the total U937 cells were shown to release $O_2^-$ in the cells.

EXAMPLE 5

Preparation of Lymphokine-Producing Human T Cell Hybridoma Line:

After treating $10^6$ cells/ml of PBL with PHA-P (manufactured by Sigma Co., Ltd.) in RPMI 1640 medium (containing 10% calf fetal serum, $5 \times 10^{-5}$M of 2-mercaptoethanol and 2 mM glutamine; hereafter simply referred to as RPMI medium) for 2 days, PHA-P bound to the cells were removed with 0.1M of N-acetylgalactosamine so that as little as possible remained.

$5 \times 10^{-5}$M of emetine hydrochloride (manufactured by Nakarai Chemical Co., Ltd.) and 0.25 μg/ml of actinomycin D (P-L Biochemical Inc.) were added to $2 \times 10^6$ cells/ml of human leukemia T cell CEM line grown in the RPMI medium. After treating at 37° C. for 2 hours, emetine hydrochloride and actinomycin D medium was removed by centrifugation.

The thus prepared PBL and CEM were mixed in a ratio of 10:1 followed by centrifugation. To the thus obtained cell pellets, 0.5 ml of 45% polyethylene glycol (PEG-4000, manufactured by Sigma Co., Ltd.) and MEM medium containing 5 μg/ml of poly-L-arginine were added. The mixture was slowly agitated for 1 minute to cause fusion. Then, MEM medium containing 10 ml of 25 mM HEPES was gradually added thereto followed by centrifugation.

RPMI medium was added to cell pellets in a cell density of $10^6$ cells/ml, 100 μl of which was mixed with 100 μl of RPMI medium containing as a feeder cell CEM ($4 \times 10^5$ cells/ml) which had been treated with a mitomycin C. The mixture was added to and cultivated on a 96-well culture plate at 37° C. for about 3 to about 4 weeks in an atmosphere of 5% $CO_2$ and 95% air. Thereafter, multiplied hybridomas were subjected to cloning by the limiting dilution method using the aforesaid mitomycin C-treated CEM as a feeder cell. After the proliferation of respective clones, various measurements were made on lymphokines.

Screening of the cloned cells using methods for the measurements of lymphokines described in Examples 6 to 10 below gave rise to clone No. D-18-23 producing MIF, clone No. D-51-5 producing MAF-G, clones No. D-81-35 and No. D-24-88 each producing MAF-0, clone No. D-42-61 producing MAF-C, and clones No. D-81-35 and No. D-24-53 each producing CSF.

Cultivation was performed at 37° C. in an atmosphere of 5% $CO_2$ and 95% air, unless otherwise indicated.

EXAMPLE 6

Measurement of MIF:

After cultivating cloned cells of lymphokine-producing human T cell hybridomas obtained in Example 5 in RPMI medium containing the same at a cell density of $10^6$ cells/ml for 48 hours, MIF activity of a 8 time-diluted solution of the thus obtained supernatant (culture supernatant (culture supernatant sample) was measured in accordance with the method shown in Example 2 above. The activity value is expressed by an inhibitory rate (%) calculated based on the following equation.

$$\text{Inhibitory Rate} = [(C-M)/C] \times 100$$

wherein M stands for the migration distance (mm) of samples of culture supernatant, and C stands for the migration distance (mm) of control sample (8-fold dilution of RPMI medium).

MIF activities of clone No. D-18-23 and CEM revealed to be 33.8% and 3.2% respectively.

Macrophage activation factor (MAF) was measured by increase in glucose consumption of macrophage, intracellular $O_2$ production of U-937 cells (human macrophage-like cell line and increase of tumor cytotoxic action. Macrophage activation factors are referred to as MAF-G, MAF-O and MAF-C, respectively.

EXAMPLE 7

Measurement of MAF-G:

The glucose consumption of guinea pig macrophage of the culture supernatant sample obtained in Example 6 was measured using liquid paraffin-induced guinea pig peritoneal exudate cells in accordance with the method described by Onozaki et al (Onozaki, K., Haga, S., Ichikawa, M., Homma, Y., Miura, K. and Hashimoto, T.; Cellular Immunology, 61, 165 (1981)). The activity value is shown by a consumption rate (%) calculated based on the following equation. The MAF activities of clone No. D-51-5 and CEM were found to be 51.5% and 25.2%, respectively.

$$\text{Consumption Rate} = (C-G)/C \times 100$$

G: glucose (%) remaining in the culture supernatant
C: glucose (%) remaining in the control sample (RMPI medium)

EXAMPLE 8

Measurement of MAF-O:

The MAF-O activity of a 2 time-diluted solution (culture supernatant sample) of the culture supernatant obtained in Example 6 was measured in accordance with the method shown in Example 4 above.

The MAF-O activities of clone Nos. D-81-35 and D-24-88 and CEM were found to be 72.0%, 27.1% and 5.0%, respectively.

EXAMPLE 9

Measurement of MAF-C:

The measurement was performed by modifying the method of Cameron et al (Cameron, D.J. and W.H. Churchill; *Journal of Clinical Investigation*, 63, 977 (1979)).

The cell density of PBL isolated from human peripheral blood by the Ficoll-Urografin method was adjusted to $2.5 \times 10^6$ cells/ml (RPMI 1640, containing 20% human serum), 200 µl of which was added and incubated in a 96-well culture plate at 37° C. for 30 minutes to 2 hours. After washing three times with RPMI medium, macrophages were attached to the bottom of the plate. Then, 200 µl of RPMI 1640 medium containing 20% human serum was added each in each of the wells followed by cultivation at 37° C. for 1 to 7 days. After discharging the supernatant and washing twice with the RPMI medium, 200 µl of a diluted sample (diluted with RPMI 1640 medium containing 20% human serum) of the culture supernatant obtained by incubating RPMI medium (with or without the addition of calf fetal serum) containing $10^6$ cells/ml of cloned cells of the lymphokine-producing human T cell hybridoma line obtained in Example 5 was added and the mixture was incubated at 37° C. for 4 to 24 hours to activate macrophages. The number of macrophages present in one well was $2 \times 10^4$ to $1 \times 10^5$.

On the other hand, target tumor cells (human leukemia T cell line TALL or human proerythroblast cell line K 562) were cultured for 20 hours in RPMI medium containing $^3$H-thymidine to obtain $^3$H-labelled target tumor cells.

To wells containing $2 \times 10^4$ to $1 \times 10^5$ of activated macrophages, $^3$H-labelled target tumor cells RPMI medium were added so as to have a ratio of the count of the activated macrophages to that of the $^3$H-labelled target tumor cells or 5 to 10, followed by incubation at 37° C. for 2 days. The supernatant was separated from the cells on a plate centrifuge and the radiation activity of the supernatant was measured with a liquid scintillation counter. The MAF-C activity value (%) was calculated based on the following equation.

$$\text{MAF-C} = (S-C)/(A-C) \times 100$$

S: radiation activity (cpm) of the supernatant
A: total radiation activity (radiation activity of $5 \times 10^5$ $^3$H-labelled target tumor cells, cpm)
C: control radiation activity (radiation activity of the supernatant obtained by incubating RPMI medium containing $10^6$ $^3$H-labelled target tumor cells at 37° C. for 2 days and then centrifuging the culture medium)

The MAF-C activities (in the case of using K 562 as a target tumor cell) of 100 time-diluted solutions or clone No. D-42-61 and CEM were found to be 55.3% and 1.8%, respectively.

EXAMPLE 10

Measurement of CSF:

The CSF activity of the culture supernatant obtained by cultivation in RPMI medium containing $5 \times 10^5$ cells/ml of cloned cells of the lymphokine-producing human T cell hybridoma line obtained in Example 5 and 5 μg/ml of ConA for 72 hours was measured by modifying the method of Tsuneoka et al (Tsuneoka, K. and M. Shikita; *FEBS LETTERS*, 77, 243 (1977)).

Myeloid cells were collected from the thighbone of 3 month-aged C3 H male mice. Among the myeloid cells, $10^5$ cells were added to a 35 mm plastic-made dish together with a McCoy 5A medium containing 0.1 ml of the culturing supernatant, 20% horse serum and 0.32% agar. Culture was performed at 37° C. for 7 days in a 5% $CO_2$ incubator and cell colonies of the formed macrophage granules were counted by a microscope. A colony having 50 cells or more was counted as 1 colony and, the activity of CSF for forming 1 colony in the dish under the conditions described above was considered 1 unit (U).

The CSF activities of clone Nos. D-81-35 and D-24-53 and CEM were found to be 60U, 150U and 3U, respectively.

EXAMPLE 11

The MIF-producing T cell hybridoma line (clone No. D-18-23) prepared in Example 5 was suspended in physiological saline in $2 \times 10^8$ cells/ml and 0.05 ml of the suspension was subcutaneously inoculated in an auto-bred golden hamster within 24 hours after birth. Then 0.05 ml of anti-lymphocyte serum (titer 320; titer was determined by measurement of agglutination to hamster thymocyte and the maximum dilution multiplication showing agglutination was made its titer) prepared by the method of S.S. Tevethia et al was subcutaneously inoculated. The anti-lymphocyte serum was consecutively administered twice a week during the feeding of the hamster.

Thirty days after, a cell mass grown under the skin was isolated in a clean bench. The weight of the cell mass was 13 g per 41 g of the body weight of the hamster.

Then, the cell mass was cut into small pieces and extruded into PBS through a stainless steel mesh to prepare a cell suspension. The total count of cells recovered in the cell suspension was $6.7 \times 10^9$, the viable cell count was $5.6 \times 10^9$ and the survival rate of the cells was 83.6%.

EXAMPLE 12

A part of the cell suspension prepared in Example 11 wa centrifugated (1000 rpm, 5 minutes). The supernatant was discharged and RPMI medium was added to the precipitated cells to suspend viable cells at a concentration of $1 \times 10^6$ cells/ml. The suspension was cultured at 37° C. for 48-hours in a flask for tissue culture. With respect to the culture supernatant, the MIF activity was measured in accordance with Example 6. As a result, the MIF activity was found to be 34.1% and the MIF-producing capacity prior to transplantation to the hamster was completely maintained.

EXAMPLE 13

100 ml of the culture supernatant prepared in Example 12 was purified by the ammonium sulfate fractionation method. The 30 to 50% saturated fraction and the 50 to 100% saturated fraction were dissolved in 2 ml and 5 ml of PBS, respectively. After dialysis against PBS overnight, the MIF activities were measured.

MIF activity was not observed with the 30 to 50% saturated fraction but MIF activity was observed with the 50 to 100% saturated fraction. The MIF activity of a 320 timediluted solution of the 50 to 100% fraction was found to be 32.5%.

The molecular weight of the MIF-containing fraction was measured by the gel filtration method (Sephadex G-75) and, found to be about 59,000. Further, the MIF activity was inhibited by 0.1M α-L-fucose.

EXAMPLE 14

The MIF-producing T cell hybridoma line (clone No. D-51-5) prepared in Example 5 was suspended in physiological saline in $2 \times 10^8$ cells/ml and 0.05 ml of the suspension was subcutaneously inoculated in an auto-bred golden hamster within 24 hours after birth. Then 0.06 mg/kg of Endoxane (trademark of cyclophosphamde, manufactured by Shionogi Pharmaceutical Co., Ltd.) was subcutaneously inoculated. Endoxane was consecutively administered at a dose of 0.12 mg/kg twice a week during the feeding of the hamster.

Forty days after, a cell mass grown under the skin was isolated in a clean bench. The weight of the tumor cell was 18 g per 63 g of the body weight of the hamster.

Then, the cell mass was cut into small pieces and extruded into PBS through a stainless mesh to prepare a cell suspension. The total count of cells recovered in the cell suspension was $7.2 \times 10^9$, the viable cell count was $6.2 \times 10^9$ and the survival rate of the cells was 86%.

EXAMPLE 15

A part of the cell suspension prepared in Example 14 was subjected to centrifugation (1000 rpm, 5 minutes). The supernatant was discharged and RPMI medium was added to the precipitated cells to suspend viable cells at a concentration of $1 \times 10^6$ cells/ml. The suspension was cultured at 37° C. for 48 hours in a flask for tissue culture. The culture supernatant was treated as in Example 7 to measure the MAF-G activity. As a result, the MAF-G activity was 51% and the MAF-G-producing capability prior to transplantation to the hamster was completely maintained.

EXAMPLE 16

The MAF-O-producing T cell hybridoma line (clone No. D-81-35) prepared in Example 5 was suspended in physiological saline in $2 \times 10^8$ cells/ml and 0.05 ml of the suspension was subcutaneously inoculated in an auto-bred golden hamster within 24 hours after birth. Then 0.05 ml of anti-lymphocyte serum was subcutaneously inoculated. The anti-lymphocyte serum was consecutively administered twice a week during the feeding of the hamster. 34 days after, a cell mass grown under the skin was isolated in a clean bench. The weight of the cell mass was 25 g per 55 g of the body weight of the hamster.

Then, the cell mass was cut into small pieces and extruded into PBS through a stainless steel mesh to prepare a cell suspension. The total count of cells recovered in the cell suspension was $1 \times 10^{10}$, the viable cell count was $8.5 \times 10^9$ and the survival rate of the cells was 85%.

EXAMPLE 17

A part of the cell suspension prepared in Example 16 was to centrifugation (1000 rpm, 5 minutes). The supernatant was discharged and 250 ml of RPMI medium was added to 2.5 $10^8$ of the precipitated cells (viable cells). The suspension was cultured at 37° C. for 48 hours in a flask of spinner type.

The culture supernatant was treated as in Example 8 to measure the MAF-O activity. As a result, the MAF-O activity was 75.1%.

EXAMPLE 18

The MAF-O-producing T cell hybridoma line (clone No. D-42-61) prepared in Example 5 was suspended in physiological saline in $1 \times 10^8$ cells/ml and 0.05 ml of the suspension was subcutaneouly inoculated in an autobred golden hamster within 24 hours after birth, which had been previously subcutaneously administered 0.05 ml of anti-lymphocyte serum. The anti-lymphocyte serum was consecutively administered twice a week during the feeding of the hamster. Twenty days after, a cell mass grown under the skin was isolated in a clean bench. The weight of the cell mass was 16 g per 35 g of the body weight of the hamster.

Then, the cell mass was cut into small pieces and extruded into PBS through a stainless steel mesh to prepare a cell suspension. The total count of cells recovered in the cell suspension was $8.8 \times 10^9$, the viable cell count was $7.9 \times 10^9$ and the survival rate of the cells was 90%.

EXAMPLE 19

A part of the cell suspension prepared in Example 18 was subjected to centrirugation (1000 rpm, 5 minutes). The supernatant was discharged and RPMI medium was added to the precipitated cells to suspend viable cells at a concentration of $1 \times 10^6$ cells/ml. The suspension was cultured at 37° C. for 48 hours in a 24 well-culture plate. The culture supernatant was treated as in Example 5 to measure the MAF-C activity. As a result, the MAF-C activity was 60.1%.

EXAMPLE 20

The CSF-producing human T cell hybridoma line (clone No. D-24-53) prepared in Example 5 was suspended in physiological saline in $1 \times 10^8$ cells/ml and 0.05 ml of the suspension was subcutaneously inoculated in an auto-bred golden hamster within 24 hours after birth. Then 0.05 ml of antilymphocyte serum was subcutaneously inoculated. The antilymphocyte serum was consecutively administered twice a week during the feeding of the hamster. 30 days after, a cell mass grown under the skin was isolated in a clean bench. The weight of the cell mass was 20 g per 45 g of the body weight of the hamster.

Then, the cell mass was cut into small pieces and extruded into PBS through a stainless steel mesh to prepare a cell suspension. The total count of cells recovered in the cell suspension was $9 \times 10^9$, the viable cell count was $7.9 \times 10^9$ and the survival rate of the cells was 88%.

EXAMPLE 21

A part of the cell suspension prepared in Example 20 was subjected to centrifugation (1000 rpm, 5 minutes). The supernatant was discharged and RPMI medium containing $5\mu g/ml$ of ConA was added to the precipitated cells to suspend viable cells at a concentration of $5 \times 10^5$ cells/ml. The suspension was cultured at 37° C. for 72 hours in a flask for tissue culture. The culture supernatant was measured by the process shown in Example 11 to measure the CSF activity. As a result, the CSF activity was 169U.

While the invention has been described in detail and with reference to specific embodiment thereof, it will be apparent to one skilled in the art that various changes and modifications can be made therein without departing from the spirit and scope thereof.

What is claimed is:

1. A process for preparing a subculturable lymphokine-producing human T cell hybridoma comprising the steps of: (1) treating a human acute leukemia cell with an irreversilbe protein synthesis inhibitor or a combination of an irreversible protein synthesis inhibitor and an irreversible RNA synthesis inhibitor so that the growth of the human acute leukemia cell is completely inhibited; (2) independently activating a human T cell with a mitogen or antigen so that blast transformation of the human T cell occurs and the desired lymphokine is produced; (3) fusing the treated human acute leukemia cell of step (1) with the activated human T cell of step (2) in the presence of a fusion accelerator; and (4) isolating the product hybridoma by incubating in a nutrient medium on which human acute leukemia cella can grow, wherein said irreversible protein synthesis inhibitor is selected from the group consisting of emetine and emetine hydrochloric acid salt and said irreversible RNA synthesis inhibitor is actinomycin D.

2. The process as claimed in claim 1, wherein said human acute leukemia cell line is T line tumor cell.

3. The process as claimed in Claim 2, wherein said human acute leukemia cell is selected from the group consisting of CEM, TALL and MOLT-4 cell line.

4. The process as claimed in claim 1, 2 or 3, wherein $10^6$ to $10^7$ cells/ml of said human acute leukemia cell line is treated with $10^{-4}$ to $10^{-5}$M of irreversible said protein synthesis inhibitor.

5. The process as claimed in claim 1, wherein said mitogen is selected from the group consisting of phytohemagglutinin-P and concanavalin A.

6. The process as claimed in claim 1, wherein $10^6$ to $10^7$ cells/ml of said irreversible acute leukemia cell line is treated with $10^{-4}$ to $10^{-5}$M of said protein synthesis inhibitor and 0.05 to 0.2 $\mu g$/ml of actinomycin D.

7. The process as claimed in claim 1, wherein said cell fusion accelerator is a polyethylene glycol having a molecular weight of 1,000 to 4,000.

8. The process as claimed in claim 1 or 7, wherein upon cell fusion, said antigen- or mitogen-treated human T cell is mixed with said human acute leukemia cell line in a cell number proportion of 1:1 to 20:1.

9. The process as claimed in claim 1 or 7, wherein upon cell fusion, said antigen- or mitogen-treated human T cell is mixed with said human acute leukemia cell line in a cell number proportion of 2:1 to 15:1.

10. The process as claimed in claim 1 or 7, wherein after cell fusion the resulting hybridoma cells are cultivated in a medium which does not permit non-protein and/or RNA synthesis inhibitor-treated human acute leukemia cell line to proliferate, thereby allowing for the isolation of the hybridoma cell.

11. The process as claimed in claim 1, wherein said cell fusion accelerator is Sendai virus (HVJ) or inactivated Sendai virus (HVT).

12. A process as claimed in claim 1, wherein the lymphokine produced by the product hybridoma is migration inhibitory factor (MIF).

13. The process as claimed in claim 1, wherein the lymphokine produced by the product hybridoma is lymphotoxin (LT).

14. The process as claimed in claim 1, wherein the product hybridoma is then subcultured in vitro or in vivo.

15. The process claimed in claim 1, further comprising the steps of: (5) transplanting said product hybridoma to a warm-blooded animal other than a human; (6) multiplying said hybridoma in said animal, and (7) cultivating the multiplied hybridomas in a nutrient medium.

16. The process as claimed in claim 15, wherein said warm-blooded animal other than a human is a hamster to which an immunosuppressive agent is administered prior to or after transplantation of the hybridoma.

17. The process as claimed in claim 16, wherein said immunosuppressive agent is anti-lymphocyte serum obtained by immunizing a rabbit with at least one member selected from the group consisting of cortison acetate, cyclophosphamide and a hamster thymocyte.

18. The process as claimed in claim 15, wherein said nutrient medium contains at least one member selected from the group consisting of sugars, amino acids, vitamins, hormones, proteins, antibiotics, growth factors and inorganic salts.

19. The process as claimed in claim 18, wherein animal serum, an antigen and/or a mitogen is incorporated into said nutrient medium.

20. The process as claimed in claim 19, wherein said animal serum is selected from the group consisting of fetal calf serum, neonatal calf serum, bovine serum, horse serum and human serum.

21. The process as claimed in claim 19, wherein said antigen is selected from the group consisting of purified tuberculin, diphtheria toxoid and herpes virus.

22. The process as claimed in claim 19, wherein said mitogen is selected from the group consisting of phytohemagglutinin, concanavalin A, staphylococcal enterotoxin A and galactose oxidase.

23. The process as claimed in claim 15, wherein said lymphokine is a macrophage migration inhibitory factor.

24. The process as claimed in claim 15, wherein said lymphokine is a macrophage activation factor.

25. The process as claimed in claim 15, wherein said lymphokine is a colony stimulating factor.

* * * * *